(12) United States Patent
Wilson et al.

(10) Patent No.: US 7,173,706 B2
(45) Date of Patent: Feb. 6, 2007

(54) APPARATUS AND METHOD FOR GAS SENSING

(75) Inventors: Andrew Wilson, Dunedin (NZ); Nicola van Leeuwen, Dunedin (NZ)

(73) Assignee: Otago Innovation Limited, Dunedin (NZ)

( * ) Notice: Subject to any disclaimer, the term of this patent is extended or adjusted under 35 U.S.C. 154(b) by 314 days.

(21) Appl. No.: 10/661,806

(22) Filed: Sep. 12, 2003

(65) Prior Publication Data

US 2004/0145743 A1    Jul. 29, 2004

Related U.S. Application Data

(63) Continuation-in-part of application No. 10/019,598, filed on Mar. 28, 2002, now abandoned.

(30) Foreign Application Priority Data

Jul. 2, 1999    (NZ)    ..................... 336552
Sep. 12, 2002    (NZ)    ..................... 521341

(51) Int. Cl.
     *G01N 21/00*    (2006.01)
(52) U.S. Cl. ..................... 356/437; 356/432
(58) Field of Classification Search ..................... None
See application file for complete search history.

(56) References Cited

U.S. PATENT DOCUMENTS 3,998,557 A * 12/1976 Javan ................ 356/434
4,516,432 A    5/1985 Hironaga et al.
4,644,153 A * 2/1987 Ida ............................ 250/225
4,824,251 A    4/1989 Slotwinski et al.
4,920,261 A * 4/1990 Bock et al. ............... 250/225
4,948,255 A * 8/1990 Watanabe ................. 356/367
5,038,029 A * 8/1991 Martens et al. ........... 250/225
5,120,131 A * 6/1992 Lukosz ..................... 356/481
5,432,610 A * 7/1995 King et al. ................ 356/432
6,050,656 A    4/2000 Farahi et al.

FOREIGN PATENT DOCUMENTS

EP      0175358 A2 * 3/1986
FR      2666164      2/1992
JP      9282577      10/1997

* cited by examiner

*Primary Examiner*—Michael P. Stafira
*Assistant Examiner*—Juan D. Valentin, II
(74) *Attorney, Agent, or Firm*—Dann, Dorfman, Herrell and Skillman, P.C.

(57) ABSTRACT

An apparatus for remote gas sensing comprising a light source, a photodetector, a gas cell containing gas or a zone through which the gas passes and through which light from the light source passes and is reflected back to the photodetector, wherein the light source, photodetector and gas cell are connected by a single polarization preserving optical fiber through which light from the light source passes to the gas cell, which light reflected back from the cell passes back through the optical fiber with a different polarization to that to the light transmitted by the light source. In one form the gas cell comprises a resonant optical cavity.

4 Claims, 1 Drawing Sheet

APPARATUS AND METHOD FOR GAS SENSING

This application is a continuation-in-part of U.S. application Ser. No. 10/019,598, filed Mar. 28, 2002, now abandoned.

FIELD OF INVENTION

The invention relates to an optical fibre delivery system for apparatus and method for sensing properties of a gas such as concentration or temperature by reference to the attenuation of light passing through the gas (trace gas sensing).

SUMMARY OF INVENTION

In broad terms in one aspect the invention comprises apparatus for remote gas sensing comprising a photodetector and a gas cell containing a gas or zone through which the gas passes and through which light from a light source passes and is reflected back to the photodetector, wherein the light source and photodetector, and the gas cell, are connected by a polarisation preserving optical fibre through which light from the source passes to the gas cell, with light reflected back from the cell passing back through the optical fibre with a different polarisation to the transmitted light.

In one form the apparatus of the invention more specifically comprises a light source, a gas cell or zone, a photodetector to receive light reflected back from the gas cell, a polarisation preserving optical fibre connecting the light source and photodetector to the gas cell, means to polarise return light exiting the gas so that it re-enters the optical fibre polarised orthogonal to the transmitted light, and means at the other end of the optical fibre to split the return light from the transmitted light and direct the return light to the photodetector.

In one form the gas cell or zone includes a mirror positioned so that gas in the gas cell passes between a point at which light enters the gas cell and said mirror, so that said mirror reflects light back through the gas and from the gas cell to the optical fibre.

In one form the gas cell or zone may comprise a resonant optical cavity containing the gas to be sensed or through which the gas passes.

In broad terms in another aspect the invention comprises a method for remote gas sensing utilising a photodetector and a gas cell or zone containing the gas or through which the gas passes and through which light from a source passes and is reflected back to the photodetector, including passing light from the source to the gas cell and back to the photodetector via a single polarisation preserving optical fibre such that the return light passes through the optical fibre with a different polarisation to that of the transmitted light.

In the apparatus and method of the invention the light source and photodetector are connected to the gas cell or zone via an arrangement including a polarisation preserving optical fibre which carries the transmitted and reflected light with different polarisations, which enables the photodetector and gas cell or zone to be remotely positioned from one another. The photodetector and associated electronics do not need to be positioned close to the gas cell or zone. The use of different polarisation for transmitted and reflected light eliminates unwanted optical interference, and enables separation of reflected from transmitted light for optical detection.

Where the gas cell comprises a resonant optical cavity, the use of circular polarised light incident on the resonant optical cavity means that the light in the retro-reflected beam directed to the photodetector can be used to frequency lock the laser source to a resonance of the optical cavity using the Pound-Drever-Hall method, so that a single transverse mode of the cavity is excited and therefore shot-to-shot variation in the decay constant is reduced and the dynamic range of the ring-down signal is maximized. In the Pound-Drever-Hall method the laser frequency is locked to a resonance of the optical cavity by frequency modulating the laser light and demodulating the light reflected from the resonant optical cavity. In the Pound-Drever-Hall method a quarter-wave plate is used so that the reflected lighted is polarised orthogonal to the incident, so that it can separated from the incident (using a polarising beam splitter) for demodulation. In the method and apparatus described here, a polarisation preserving optical fibre is placed between the light source and the resonant optical cavity so that the light reflected from the resonant optical cavity propagates back through the optical fibre with a polarisation which is orthogonal to the light incident on the cavity. Therefore, the Pound-Drever-Hall frequency stabilisation method can be used even when the resonant optical cavity is placed at the opposite end of a polarisation preserving fibre to a laser source.

BRIEF DESCRIPTION OF THE DRAWINGS

The invention is further described with reference to the accompanying drawings by way of example and without intending to be limiting in which.

DETAILED DESCRIPTION OF PREFERRED FORMS

Figure 1:
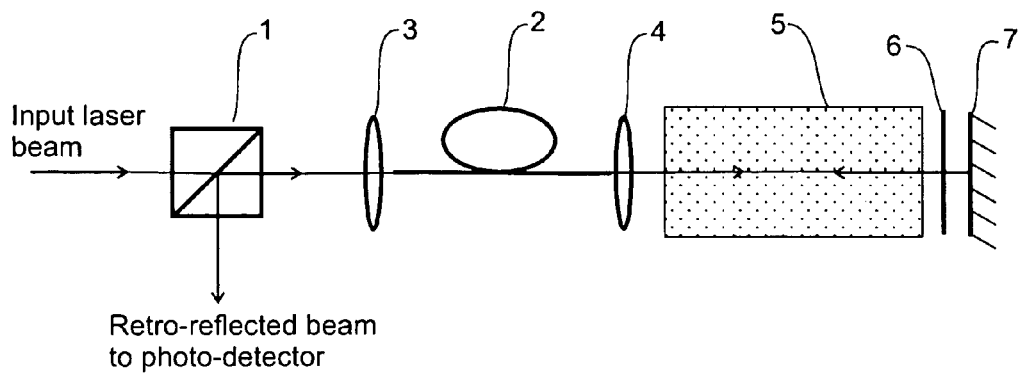
FIG. 1 schematically illustrates one preferred form of gas sensing apparatus, FIG. 2 schematically illustrates another preferred form of gas sensing apparatus using a resonant optical cavity as the gas cell.

Referring to FIG. 1 light from a source such as a laser passes through a polarising beam splitter 1 which is oriented to linearly polarise the light parallel to one of the two polarisation maintaining axis of a polarisation preserving single-mode optical fibre 2. The light is launched into the polarisation preserving fibre by a lens 3, and propagates through the optical fibre maintaining its polarisation state.

Upon exiting the fibre, the light is collimated by a second lens 4, and propagates through a gas sample region or cell 5, in a double pass configuration using a quarter-wave retarder 6 or other polarising device, and retro-reflecting mirror 7. Some of the light is absorbed by the gas as it propagates through the gas sample, and this is used to determine properties of the sample, such as concentration and temperature.

Quarter-wave retarder 6 is oriented to change the polarisation state of the transmitted light from linear to pure circular. After retro-reflection by the mirror 7, the return light then passes back through the quarter-wave retarder 6, which changes the polarisation state of the light from circular back to linear, but with an orientation perpendicular to that of the forward propagating (transmitted) light. The mirror 7 is aligned so that the reflected light is launched back into the fibre, but because it is linearly polarised perpendicular to the forward propagating light, the reflected light is polarised parallel to the other polarisation preserving axis of the optical fibre. This means that the forward and retro-reflected light propagates simultaneously through the optical fibre, but they have orthogonal linear polarisation states.

Upon exiting the fibre, the retro-reflected light is separated from the forward propagating light by the polarising beam splitter 1, and directed to the photodetector where its intensity is measured.

Figure 2:
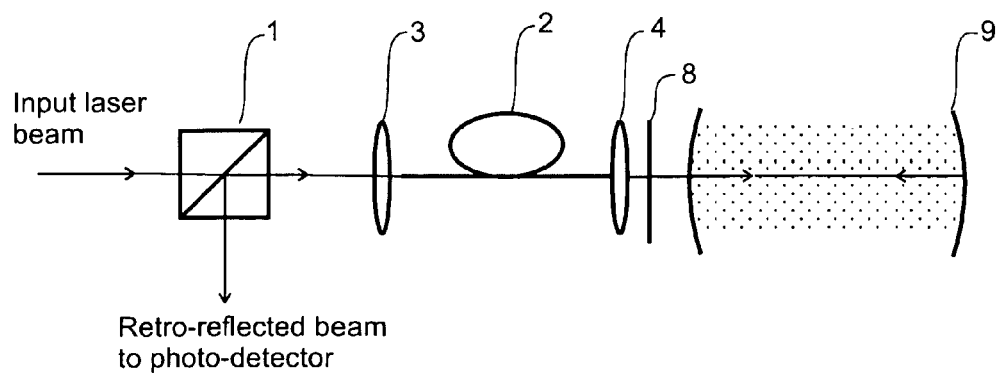

In the alternative form of FIG. 2 light from a source such as a laser similarly passes through a polarising beam splitter 1 which linearly polarises the light parallel to one of the two polarisation maintaining axes of polarisation preserving single-mode optical fibre 2, and the light is launched into the fibre by lens 3. Upon exiting the fibre, the light is collimated and mode matched for maximum coupling into the gas cell resonant optical cavity by a second lens (or lenses) 4. The light then propagates through a quarter-wave retarder 8 oriented to circular polarise the light, or other polarising device, and enters the gas cell 9 which in this form comprises a resonant optical cavity containing a sample of gas or through which the gas is flowing. Within the optical cavity which is typically comprised of a pair of highly reflective mirrors as known, the intra-cavity light undergoes multiple passes through the gas sample which enhances the attenuation of the light. The attenuation is determined by the cavity ring-down time (the characteristic time over which the light decays from the cavity) and this can be used to determine properties of the gas sample, such as concentration and temperature. The light source may be briefly switched off and the cavity ring-down time determined before the light is switched on again. Alternatively the wavelength of the light may be moved off resonance with the optical cavity for the duration of the cavity ring-down or a pulsed laser may be used with cavity decay occurring after each laser pulse. A range of wavelengths may be used to provide additional information.

The quarter-wave retarder 8 is oriented to change the polarisation state of the transmitted light from linear to pure circular. After retro-reflection by the resonant optical cavity 9, the return light then passes back through the quarter-wave retarder 8, which changes the polarisation state of the light from circular back to linear, but with an orientation perpendicular to that of the forward propagating (transmitted) light. The resonant optical cavity 9 is aligned so that the reflected light is launched back into the fibre, but because it is linearly polarised perpendicular to the forward propagating light, the reflected light is polarised parallel to the other polarisation preserving axis of the optical fibre. The forward and retro-reflected light propagates simultaneously through the optical fibre, but with orthogonal linear polarisation states. Upon exiting the fibre, the retro-reflected light is again separated from the forward propagating light by polarising beam splitter 1, and directed to the photodetector where its intensity is measured.

The preferred forms illustrated are described by way of example. Alternative arrangements utilising in the concept of the invention are possible. For example in the embodiment of FIG. 1 an alternative arrangement light exiting the optical fibre may be allowed to diverge by removing the collimating lens 4, and then retro-reflected using a spherical mirror placed a small distance equal to the radius of curvature of the mirror. In the embodiment of FIG. 2 the optical cavity may take any optical resonator form (e.g. a ring cavity). In both cases separate optical components may be replaced by thin film or optical fibre based elements.

The gas cell may be positioned in a hostile environment (for example hot or toxic), a cramped environment (for example within a compact machine), or a very distant location (for example on top of a smoke stack).

The foregoing describes the invention including a preferred form thereof. Alterations and modifications as will be obvious to those skilled in the art are intended to be incorporated within the scope hereof as defined in the accompanying claims.

The invention claimed is:

1. A method for remote gas sensing utilising a light source, a photodetector and a gas cell or zone containing gas or through which gas passes and through which light from the light source passes and is reflected back to the photodetector, including passing light from the source to a gas cell or zone comprising a resonant optical cavity, and back to the photodetector via a single polarisation preserving optical fibre, causing the returned light to pass through the optical fibre with a different polarisation to that of the transmitted light splitting, between the light source and the optical fibre, the returned light from the transmitted light and directing the returned light to the photodetector, and sensing the gas via the cavity ring-down time of the gas in the resonant cavity.

2. A method according to claim 1 further comprising polarising the returned light exiting the gas so that it re-enters the optical fibre polarised orthogonal to the transmitted light.

3. A method according to claim 1 including causing the gases to pass in the gas cell or zone between a mirror and a point at which light enters the gas cell, so that said mirror reflects light back through the gas and from the gas cell to the optical fibre.

4. A method according to any one of claims 1 to 3 wherein the light source and photodetector are positioned remotely to the gas cell or zone.

* * * * *